United States Patent
Perkins et al.

(10) Patent No.: US 11,851,719 B2
(45) Date of Patent: Dec. 26, 2023

(54) LINEAGE REPORTER SYNTHETIC CHROMOSOMES AND METHODS OF USE

(71) Applicant: SynPloid Biotek, LLC, Savannah, GA (US)

(72) Inventors: Edward Perkins, Savannah, GA (US); Amy Greene, Savannah, GA (US)

(73) Assignee: CarryGenes Bioengineering, LLC, Savannah, GA (US)

( * ) Notice: Subject to any disclaimer, the term of this patent is extended or adjusted under 35 U.S.C. 154(b) by 175 days.

(21) Appl. No.: 16/120,638

(22) Filed: Sep. 4, 2018

(65) Prior Publication Data

US 2019/0071738 A1 Mar. 7, 2019

Related U.S. Application Data

(60) Provisional application No. 62/554,502, filed on Sep. 5, 2017.

(51) Int. Cl.

| | | |
|---|---|---|
| C07H 21/04 | (2006.01) | |
| C12Q 1/6897 | (2018.01) | |
| C12N 5/0735 | (2010.01) | |
| C12N 15/85 | (2006.01) | |
| C12N 5/074 | (2010.01) | |
| C07K 1/13 | (2006.01) | |

(52) U.S. Cl.
CPC ......... C12Q 1/6897 (2013.01); C12N 5/0606 (2013.01); C12N 5/0696 (2013.01); C12N 15/85 (2013.01); C07K 1/13 (2013.01); C07K 2319/60 (2013.01); C12N 2510/00 (2013.01); C12N 2800/208 (2013.01); C12N 2800/30 (2013.01); C12N 2830/008 (2013.01)

(58) Field of Classification Search
None
See application file for complete search history.

(56) References Cited

U.S. PATENT DOCUMENTS

| | | | |
|---|---|---|---|
| 9,273,324 B2 | 3/2016 | Belmont | |
| 2002/0160410 A1 | 10/2002 | Hadlaczky et al. | |
| 2004/0096891 A1 | 5/2004 | Bennett | |
| 2005/0181506 A1 | 8/2005 | Perkins et al. | |
| 2007/0004002 A1 | 1/2007 | Okazaki | |
| 2008/0216185 A1* | 9/2008 | Chesnut | C12N 15/1082 800/21 |
| 2011/0318832 A1 | 12/2011 | Cech et al. | |
| 2012/0064578 A1* | 3/2012 | Perkins | C12N 15/902 435/91.41 |
| 2012/0093785 A1 | 4/2012 | Oshimura et al. | |
| 2014/0295501 A1 | 10/2014 | Katona et al. | |
| 2018/0010150 A1* | 1/2018 | Perkins | C12N 15/90 |

FOREIGN PATENT DOCUMENTS

| | | |
|---|---|---|
| EP | 2218786 A4 | 6/2011 |
| EP | 2522725 B1 | 10/2016 |
| EP | 1559782 B1 | 12/2016 |
| WO | 9740183 A2 | 10/1997 |
| WO | 0018941 A1 | 4/2000 |
| WO | 02096923 B1 | 5/2004 |
| WO | 2013052915 A2 | 4/2013 |

OTHER PUBLICATIONS

Basu, J., "Artificial and Engineered Chromosomes: Non-Integrating Vectors for Gene Therapy." Trends in Molecular Medicine, Elsevier Current Trends, vol. 11 (5), pp. 251-258 (2005).
Greene, et al., 2019, "Engineering Synthetic Chromosomes by Sequential Loading of Multiple Genomic Payloads over 100 Kilobase Pairs in Size." Molecular Therapy: Methods & Clinical Development, 13:463-473.
Ikeno, M et al., "Construction of YAC-based mammalian artificial chromosomes", Nature Biotechnology, (19980500), vol. 16, No. 5, pp. 431-439, XP009060040.
International Search Report and Written Opinion dated Dec. 17, 2018 in PCT/US18/49426.
Katoh, et al., (2004) "Construction of a novel human artificial chromosome vector for gene delivery." Biochem. Biophys. Res. Comm. 321:280-290.
Kazuki, et al., "Refined human artificial chromosome vectors for gene therapy and animal transgenesis." Gene Therapy, vol. 18(4):384-393 (2010).
Kazuki, Y et al., "Human Artificial Chromosomes for Gene Delivery and the Development of Animal Models", Molecular Therapy, (2011) 19(9):1591-1601. doi:10.1038/mt.2011.136, XP055581607.
Kouprina et al., (2013) "A new generation of human artificial chromosomes for functional genomics and gene therapy", Cell Mol Life Sci., vol. 70, No. 7, pp. 1135-1148, XP055470579.
Kouprina, et al., (2014) "Human Artificial Chromosome-Based Gene Delivery Vectors for Biomedicine and Biotechnology." Expert Opinion on Drug Delivery. 11(4):517-535.
Kurosaki, et al., "Integration-free and stable expression of FVIII using a human artificial chromosome." Journal of Human Genetics, vol. 56 (10), pp. 727-733 (2011).
Lindenbaum et al., "A mammalian artificial chromosome engineering system (ACE System) applicable to biopharmaceutical protein production, transgenesis and gene-based cell therapy," Nucleic Acids REsearch, (2004), vol. 32, No. 21, pp. e172 1-15.
Martella, et al., "Mammalian Synthetic Biology: Time for Big MACS," ACS Synthetic Biology, vol. 5, No. 10, pp. 1040-1049.
Ren, X et al., "A Novel Human Artificial Chromosome Vector Provides Effective Cell Lineage-Specific Transgene Expression in Human Mesenchymal Stem Cells", Stem Cells, (Nov. 1, 2005), vol. 23, No. 10, doi:10.1634/stemcells.2005-0021, pp. 1608-1616, XP055473399.

(Continued)

*Primary Examiner* — Celine X Qian
(74) *Attorney, Agent, or Firm* — Susan J. Myers Fitch

(57) ABSTRACT

The field of the invention encompasses synthetic chromosome compositions and methods that allow single cell spatiotemporal analysis in response to differentiation cues and labeling of transplanted cells to monitor the fate and function of such cells in the patient recipient.

1 Claim, 1 Drawing Sheet

(56) References Cited

OTHER PUBLICATIONS

Rocchi, et al., (2010) "*Escherichia coli*-Cloned CTFR Loci Relevant for Human Artificial Chromosome Therapy." Human Gene Therapy, 21:1077-1092.

Shitara, et al., 2008, "Telomerase-mediated life-span extension of human primary fibroblasts by human artificial chromosome (HAC) vector." Biochem. Biophys. Res. Commun. 369(3):807-11.

Takiguchi, et al., "A Novel and Stable Mouse Artificial Chromosome Vector." ACS Synthetic Biology, vol. 3 (12), pp. 903-914 (2014).

Teruhiko Suzuki et al., "A Novel System for Simultaneous or Sequential Integral of Multiple Gene-Loading Vectors into a Defined Site of a Human Artificial Chromosome," PLOS ONE, vol. 9, No. 10, pp. 1-9.

Toth, et al., "Novel Method to Load Multiple Genes onto a Mammalian Artificial Chromosome." Plos One, Public Library of Science, US, vol. 9 (1), pp. e85565-1 (2014).

Vanderbyl, S et al., "Transfer and Stable Transgene Expression of a Mammalian Artificial Chromosome into Bone Marrow-Derived Human Mesenchymal Stem Cells", Stem Cells, (20040500), vol. 22, No. 3, doi:doi:10.1634/stemcells.22-3-324, pp. 324-333, XP002506658.

Yamaguchi, et al., 2011 "A Method for Producing Transgenic Cells Using a Multi-Integrase System on a Human Artificial Chromosome Vector." PLoS ONE 6(2): e17267. https://doi.org/10.1371/journal.pone.0017267.

Giel-Moloney et al., "Ubiquitous and uniform in vivo fluorescence in ROSA26-EGFP BAC transgenic mice," Genesis, Wiley-Liss,Feb. 1, 2007, pp. 83-89, vol. 45, No. 2.

Herz et al., "Live monitoring of small vessels during development and disease using the flt-1 promoter element," Basic Research in Cardiology, Steinkopff-Verlag, DA, Mar. 1, 2012, pp. 1-14, vol. 107, No. 2.

Brenda Grimes and Zoia Monaco, "Artificial and Engineered Chromosomes: Developments and Prospects for Gene Therapy," Chromosoma, (2005), 114:230-241.

Bruce Bunnell, et al., "Development of Mammalian Artificial Chromosomes for the Treatment of Genetic Diseases: Sandhoff and Krabbe Diseases," Expert Opin. Biol. Therapy (2005) 5(2):95-206.

Tomohiro Tsuduki, et al., "An Artificially Constructed De Novo Human Chromosome Behaves Almost Identically to Its Natural Counterpart during Metaphase and Anaphase in Living Cells," Molecular and Cellular Biology (2006), vol. 26, No. 20, p. 7682-7695.

Yueju Wang, et al., "Recombinase Technology: Applications and Possibilities," Plant Cell Rep., (2011), 30:267-285.

\* cited by examiner

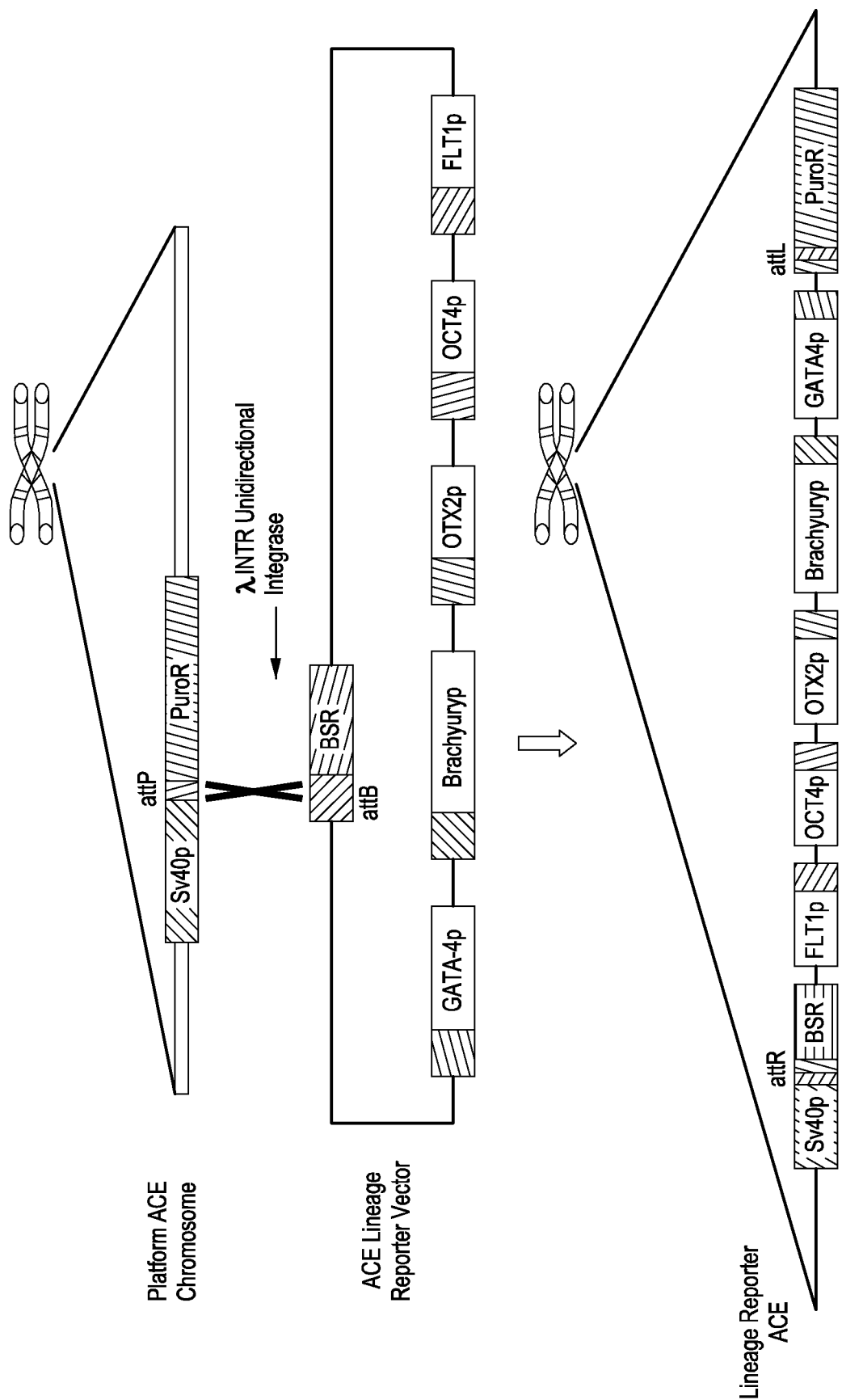

LINEAGE REPORTER SYNTHETIC CHROMOSOMES AND METHODS OF USE

CROSS REFERENCE TO RELATED APPLICATIONS

This application claims the benefit of U.S. Provisional Patent Application No. 62/554,502, filed Sep. 5, 2017 and is incorporated herein by reference.

FIELD OF THE INVENTION

The field of the invention encompasses synthetic chromosome compositions and methods that allow single cell spatiotemporal analysis in response to differentiation cues and labeling of transplanted cells to monitor the fate and function of such cells in the patient recipient.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Progress in analysis of single cells to define fundamental differences in cell diversity driven by pathways responding to environmental cues has been held back by the absence of one indispensable tool required to address complex polygenicity and/or delivery of large genetic payloads: a stable, non-integrating, self-replicating and biocompatible intracellular platform. Synthetic chromosomes provide the breakthrough in biological bandwidth required to introduce large genetic payloads supporting development of complex cell-based biosensors.

Thus, there is a need in the art for compositions and methods that allow one to track differentiating cells from, e.g., an embryoid body, for spatiotemporal analysis of transplanted cells to monitor their fate and function in a patient recipient. The present invention provides solutions to this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description, including those aspects illustrated in the accompanying drawings and defined in the appended claims.

The ability to define the status of a single cell within a diverse population has been obstructed by the absence of tools that have the capability to delineate multiple states within a single population. Synthetic chromosomes rationally engineered to contain select large genetic payloads without alteration of the host chromosomes significantly advances development of complex cell-based biosensors. Such synthetic chromosomes can be used in vitro to screen the effect of exogenous stimuli on cell fate and/or pathway activation and in vivo to establish the effect of exposure to exogenous or endogenous signals on development with single cell resolution.

In some embodiments, the present invention provides a synthetic chromosome engineered to allow single cell spatiotemporal analysis in response to differentiation cues and to label transplanted cells to monitor their fate and function in the patient recipient. In some aspects of this embodiment, the synthetic chromosome comprises a plurality of reporter genes driven by lineage-specific promoters. In some aspects, the lineage-specific promoters include promoters for Oct4 (pluripotency), GATA4 (endoderm), Brachyury (mesoderm), and Otx2 (ectoderm).

In yet other embodiments, the present invention provides an induced pluripotent stem cell comprising a synthetic chromosome comprising lineage-specific promoters linked to different fluorescent markers to provide readout for cell lineage fate determination.

In still other embodiments, the present invention provides a method for isolating cells of different lineages comprising transferring a synthetic chromosome comprising lineage specific promoters into pluripotent stem cells, differentiating the pluripotent stem cells into embryoid bodies, dissociating the embryoid bodies, and sorting and isolating cells of each lineage.

In another embodiment, the present invention provides a synthetic chromosome comprising a plurality of reporter genes driven by damage- or toxin-responsive promoters. In some aspects, the promoters are promoters responsive to irradiation, heavy metals, and the like.

In yet another embodiment, the present invention provides a method of tracking transplanted cells in an animal comprising the steps of transforming cells to be transplanted with a synthetic chromosome comprising a reporter gene, and tracking the reporter gene. In some aspects, the synthetic chromosome may also comprise an expression cassette to deliver a therapeutic peptide.

These and other aspects and uses of the invention will be described in the detailed description.

BRIEF DESCRIPTION OF THE FIGURES

FIG. 1 is a graphic illustration of a lineage reporter synthetic chromosome. The lineage reporter synthetic chromosome was engineered to contain five lineage specific promoters linked to unique fluorescent reporters to create a multifunctional cell-based biosensor.

DETAILED DESCRIPTION OF THE INVENTION

The methods described herein may employ, unless otherwise indicated, conventional techniques and descriptions of molecular biology (including recombinant techniques), cell biology, biochemistry, and cellular engineering technology, all of which are within the skill of those who practice in the art. Such conventional techniques include oligonucleotide synthesis, hybridization and ligation of oligonucleotides, transformation and transduction of cells, engineering of recombination systems, creation of transgenic animals and plants, and human gene therapy. Specific illustrations of suitable techniques can be had by reference to the examples herein. However, equivalent conventional procedures can, of course, also be used. Such conventional techniques and descriptions can be found in standard laboratory manuals such as *Genome Analysis: A Laboratory Manual Series* (Vols. I-IV) (Green, et al., eds., 1999); *Genetic Variation: A*

*Laboratory Manual* (Weiner, et al., eds., 2007); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); *Protein Methods* (Bollag et al., John Wiley & Sons 1996); *Nonviral Vectors for Gene Therapy* (Wagner et al. eds., Academic Press 1999); *Viral Vectors* (Kaplift & Loewy, eds., Academic Press 1995); *Immunology Methods Manual* (Lefkovits ed., Academic Press 1997); *Gene Therapy Techniques, Applications and Regulations From Laboratory to Clinic* (Meager, ed., John Wiley & Sons 1999); M. Giacca, *Gene Therapy* (Springer 2010); *Gene Therapy Protocols* (LeDoux, ed., Springer 2008); *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011); *Essential Stem Cell Methods*, (Lanza and Klimanskaya, eds., Academic Press 2011); *Stem Cell Therapies: Opportunities for Ensuring the Quality and Safety of Clinical Offerings: Summary of a Joint Workshop* (Board on Health Sciences Policy, National Academies Press 2014); *Essentials of Stem Cell Biology*, Third Ed., (Lanza and Atala, eds., Academic Press 2013); and *Handbook of Stem Cells*, (Atala and Lanza, eds., Academic Press 2012), all of which are herein incorporated by reference in their entirety for all purposes. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by the appended claims.

Note that as used in the present specification and in the appended claims, the singular forms "a," "and," and "the" include plural referents unless the context clearly dictates otherwise. Thus, for example, reference to "a composition" refers to one or mixtures of compositions, and reference to "an assay" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value between the upper and lower limit of that range and any other stated or intervening value in that stated range is encompassed within the invention. The upper and lower limits of these smaller ranges may independently be included in the smaller ranges, subject to any specifically excluded limit in the stated range. Where the stated range includes both of the limits, ranges excluding either one of those included limits are also included in the invention.

In the following description, numerous specific details are set forth to provide a more thorough understanding of the present invention. However, it will be apparent to one of ordinary skill in the art upon reading the specification that the present invention may be practiced without one or more of these specific details. In other instances, well-known features and procedures well known to those skilled in the art have not been described in order to avoid obscuring the invention.

Definitions

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

"Binding" as used herein (e.g., with reference to an nucleic acid-binding domain of a polypeptide) refers to a non-covalent interaction between a polypeptide and a nucleic acid. While in a state of non-covalent interaction, the polypeptide and nucleic acid are said to be "associated", "interacting", or "binding". Binding interactions are generally characterized by a dissociation constant (Kd) of less than $10^{-6}$ M to less than $10^{-18}$ M. "Affinity" refers to the strength of binding, increased binding affinity being correlated with a lower Kd.

By "binding domain" it is meant a polypeptide or protein domain that is able to bind non-covalently to another molecule. A binding domain can bind to, for example, a DNA molecule (a DNA-binding protein), an RNA molecule (an RNA-binding protein) and/or a protein molecule (a protein-binding protein).

A "centromere" is any nucleic acid sequence that confers an ability of a chromosome to segregate to daughter cells through cell division. A centromere may confer stable segregation of a nucleic acid sequence, including a synthetic chromosome containing the centromere, through mitotic and meiotic divisions. A centromere does not necessarily need to be derived from the same species as the cells into which it is introduced, but preferably the centromere has the ability to promote DNA segregation in cells of that species. A "dicentric" chromosome is a chromosome that contains two centromeres. A "formerly dicentric chromosome" is a chromosome that is produced when a dicentric chromosome fragments. A "chromosome" is a nucleic acid molecule— and associated proteins—that is capable of replication and segregation in a cell upon division of the cell. Typically, a chromosome contains a centromeric region, replication origins, telomeric regions and a region of nucleic acid between the centromeric and telomeric regions. An "acrocentric chromosome" refers to a chromosome with arms of unequal length.

A "coding sequence" or a sequence that "encodes" a peptide is a nucleic acid molecule that is transcribed (in the case of DNA) and translated (in the case of mRNA) into a polypeptide in vivo when placed under the control of appropriate control sequences. The boundaries of the coding sequence typically are determined by a start codon at the 5' (amino) terminus and a translation stop codon at the 3' (carboxy) terminus.

The term DNA "control sequences" refers collectively to promoter sequences, polyadenylation signals, transcription termination sequences, upstream regulatory domains, origins of replication, internal ribosome entry sites, enhancers, and the like, which collectively provide for the replication, transcription and translation of a coding sequence in a recipient cell. Not all of these types of control sequences need to be present so long as a selected coding sequence is capable of being replicated, transcribed and translated in an appropriate host cell.

"Endogenous chromosomes" refer to chromosomes found in a cell prior to generation or introduction of a synthetic chromosome.

As used herein, "euchromatin" refers to chromatin that stains diffusely and that typically contains genes, and "heterochromatin" refers to chromatin that remains unusually condensed and is thought to be transcriptionally inactive. Highly repetitive DNA sequences (satellite DNA) are usually located in regions of the heterochromatin surrounding the centromere.

The terms "heterologous DNA" or "foreign DNA" (or "heterologous RNA" or "foreign RNA") are used interchangeably and refer to DNA or RNA that does not occur naturally as part of the genome in which it is present, or is found in a location or locations and/or in amounts in a genome or cell that differ from that in which it occurs in nature. Examples of heterologous DNA include, but are not limited to, DNA that encodes a gene product or gene product(s) of interest. Other examples of heterologous DNA include, but are not limited to, DNA that encodes traceable marker proteins as well as regulatory DNA sequences.

"Operably linked" refers to an arrangement of elements where the components so described are configured so as to perform their usual function. Thus, control sequences operably linked to a coding sequence are capable of effecting the expression of the coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome), and may still have interactions resulting in altered regulation.

A "promoter" or "promoter sequence" is a DNA regulatory region capable of binding RNA polymerase in a cell and initiating transcription of a polynucleotide or polypeptide coding sequence such as messenger RNA, ribosomal RNAs, small nuclear or nucleolar RNAs or any kind of RNA transcribed by any class of any RNA polymerase I, II or III.

"Recognition sequences" are particular sequences of nucleotides that a protein, DNA, or RNA molecule, or combinations thereof (such as, but not limited to, a restriction endonuclease, a modification methylase or a recombinase) recognizes and binds. For example, a recognition sequence for Cre recombinase is a 34 base pair sequence containing two 13 base pair inverted repeats (serving as the recombinase binding sites) flanking an 8 base pair core and designated loxP (see, e.g., Sauer, Current Opinion in Biotechnology, 5:521-527 (1994)). Other examples of recognition sequences, include, but are not limited to, attB and attP, attR and attL and others that are recognized by the recombinase enzyme bacteriophage Lambda Integrase. The recombination site designated attB is an approximately 33 base pair sequence containing two 9 base pair core-type Int binding sites and a 7 base pair overlap region; attP is an approximately 240 base pair sequence containing core-type Int binding sites and arm-type Int binding sites as well as sites for auxiliary proteins IHF, FIS, and Xis (see, e.g., Landy, Current Opinion in Biotechnology, 3:699-7071 (1993)).

A "recombinase" is an enzyme that catalyzes the exchange of DNA segments at specific recombination sites. An integrase refers to a recombinase that is usually derived from viruses or transposons, as well as perhaps ancient viruses. "Recombination proteins" include excisive proteins, integrative proteins, enzymes, co-factors and associated proteins that are involved in recombination reactions using one or more recombination sites (see, Landy, Current Opinion in Biotechnology, 3:699-707 (1993)). The recombination proteins used in the methods herein can be delivered to a cell via an expression cassette on an appropriate vector, such as a plasmid, and the like. In other embodiments, recombination proteins can be delivered to a cell in protein form in the same reaction mixture used to deliver the desired nucleic acid(s). In yet other embodiments, the recombinase could also be encoded in the cell and expressed upon demand using a tightly controlled inducible promoter.

"Ribosomal RNA" (rRNA) is the specialized RNA that forms part of the structure of a ribosome and participates in the synthesis of proteins. Ribosomal RNA is produced by transcription of genes which, in eukaryotic cells, are present in multiple copies. In human cells, the approximately 250 copies of rRNA genes (i.e., genes which encode rRNA) per haploid genome are spread out in clusters on at least five different chromosomes (chromosomes 13, 14, 15, 21 and 22). In human cells, multiple copies of the highly conserved rRNA genes are located in a tandemly arranged series of rDNA units, which are generally about 40-45 kb in length and contain a transcribed region and a nontranscribed region known as spacer (i.e., intergenic spacer) DNA which can vary in length and sequence.

As used herein the term "selectable marker" refers to a gene introduced into a cell, particularly in the context of this invention into cells in culture, that confers a trait suitable for artificial selection. General use selectable markers are well-known to those of ordinary skill in the art. In preferred embodiments, selectable markers for use in a human synthetic chromosome system should be non-immunogenic in the human and include, but are not limited to: human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in $CD34^+$ cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); and Cytidine deaminase (CD; selectable by Ara-C). Drug selectable markers such as puromycin, hygromycin, blasticidin, G418, tetracycline may also be employed. In addition, using FACs sorting, any fluorescent marker gene may be used for positive selection, as may chemiluminescent markers (e.g. Halotags), and the like.

"Site-specific recombination" refers to site-specific recombination that is effected between two specific sites on a single nucleic acid molecule or between two different molecules that requires the presence of an exogenous protein, such as an integrase or recombinase. Certain site-specific recombination systems can be used to specifically delete, invert, or insert DNA, with the precise event controlled by the orientation of the specific sites, the specific system and the presence of accessory proteins or factors. In addition, segments of DNA can be exchanged between chromosomes (chromosome arm exchange).

"Synthetic chromosomes" (also referred to as "artificial chromosomes") are nucleic acid molecules, typically DNA, that have the capacity to accommodate and express heterologous genes and that stably replicate and segregate alongside endogenous chromosomes in cells. A "mammalian synthetic chromosome" refers to chromosomes that have an active mammalian centromere(s). A "human synthetic chromosome" refers to a chromosome that includes a centromere that functions in human cells and that preferably is produced in human cells. For exemplary artificial chromosomes, see, e.g., U.S. Pat. Nos. 8,389,802; 7,521,240; 6,025,155; 6,077,697; 5,891,691; 5,869,294; 5,721,118; 5,712,134; 5,695,967; and 5,288,625 and published International PCT application Nos, WO 97/40183 and WO 98/08964.

The terms "subject", "individual" or "patient" may be used interchangeably herein and refer to a mammal, and in some embodiments, a human.

A "vector" is a replicon, such as plasmid, phage, viral construct, cosmid, bacterial artificial chromosome, P-1 derived artificial chromosome or yeast artificial chromosome to which another DNA segment may be attached. In some instances a vector may be a chromosome such as in the case of an arm exchange from one endogenous chromosome engineered to comprise a recombination site to a synthetic chromosome. Vectors are used to transduce and express a DNA segment in cell.

The Invention

The ability to define the status of a single cell within a diverse population has been obstructed by the absence of tools that have the capability to delineate multiple states within a single population. Synthetic chromosomes rationally engineered to contain select large genetic payloads without alteration of the host chromosomes significantly advance development of complex cell-based biosensors. These synthetic chromosomes can be used in vitro to screen the effect of exogenous stimuli on cell fate and/or pathway activation and in vivo to establish the effect of exposure to exogenous or endogenous signals on development with single cell resolution. In one embodiment, the present invention encompasses compositions and methods to allow one to allow single cell spatiotemporal analysis in response to differentiation cues and to label transplanted cells to monitor their fate and function in the patient recipient. In another embodiment, the present invention provides an induced pluripotent stem cell comprising a synthetic chromosome comprising lineage specific promoters linked to different fluorescent markers to provide readout for cell lineage fate determination. In yet another embodiment, the present invention provides a method for differentiating into embryoid bodies induced pluripotent stem cells comprising a synthetic chromosome where the synthetic chromosome comprises lineage specific promoters, dissociating the embryoid bodies, and sorting and isolating cells of each lineage.

The ability to define the status of a single cell within a diverse population has been hampered by the absence of tools that have the capability to delineate multiple states within a single population. A synthetic chromosome system has been developed that has the bandwidth to allow loading of large genomic regions, including endogenous regulatory elements. The present invention provides a synthetic chromosome as a cell-based biosensor for in situ analysis of single cell status within a diverse population in response to specific signals. The novel synthetic chromosome allows identification of the fate and/or isolation of specific cells within a diverse population with single cell resolution following exposure to exogenous stimuli.

Briefly, the lineage reporter synthetic chromosome is transferred into human induced pluripotent stem cells (iPSCs) using standard protocols (such as those described in, e.g., U.S. Ser. No. 15/548,236; PCT/US2017/027102; PCT/US2017/027069; PCT/US2017/027270, all of which are incorporated herein for all purposes). Human iPSCs are differentiated into embryoid bodies (EBs) and the EBs are monitored by confocal microscopy over time to confirm the presence of endo-, meso- and ectoderm lineages. Thus, the present invention provides a novel tool for single cell spatiotemporal analysis.

The ability to purify single viable cells from unique lineages within a diverse population is demonstrated by flow sorting and subsequent microscopic analysis of resultant cultures. iPSCs are differentiated into EBs. The EBs are dissociated and cells of each lineage are isolated using flow sorting. Microscopic imaging and quantitative RT-PCR, to quantify expression of lineage specific markers, assesses the degree of cell enrichment.

Additionally, the present invention provides an engineered synthetic chromosome utilizing mouse regulatory elements used to generate transgenic mice wherein the fate of single cells within a tissue and/or the organism is monitored following exposure to specific signals. Additionally, the present invention provides engineered synthetic chromosomes containing reporter genes driven by damage or toxins (e.g., irradiation, heavy metals, etc.) responsive promoters. The present invention further provides a human synthetic chromosome to be used deliver stem cell-based therapeutics for regenerative or oncologic medicine, as well as containing reporters to allow tracking the transplanted cells.

FIG. 1 shows a lineage reporter synthetic chromosome. The lineage reporter synthetic chromosome was engineered to contain five lineage specific promoters linked to unique fluorescent reporters to create a multifunctional cell-based biosensor; GATA4 promoter linked to E2-Crimson (far red; endoderm), Brachyury promoter linked to BFP (mesoderm); OTX2 promoter linked to YFP (ectoderm), OCT4 promoter linked to humanized *Renilla* (hr) GFP (pluripotency), and FLT1 promoter linked to mCherry (vascular endothelium, brain endothelium).

Synthetic Chromosome Producing Cells

In some embodiments, the cells to be engineered and/or produce the synthetic chromosome can be cells that naturally occur in a subject (human patient, animal or plant) in which the genes or regulatory sequences from the synthetic chromosome will ultimately be expressed. Such cells can be primary-culture cell lines established for the purpose of synthetic chromosome production specific for an individual. In other embodiments, the cells to be engineered and/or produce the synthetic chromosome are from an established cell line. A wide variety of cell lines for tissue culture are known in the art. Examples of cell lines include but are not limited to human cells lines such as 293-T (embryonic kidney), 721 (melanoma), A2780 (ovary), A172 (glioblastoma), A253 (carcinoma), A431 (epithelium), A549 (carcinoma), BCP-1 (lymphoma), BEAS-2B (lung), BR 293 (breast), BxPC3 (pancreatic cancinoma), Cal-27 (tongue), COR-L23 (lung), COV-434 (ovary), CML T1 (leukemia), DUI45 (prostate), DuCaP (prostate), FM3 (lymph node), H1299 (lung), H69 (lung), HCA2 (fibroblast), HEK0293 (embryonic kidney), HeLa (cervix), HL-60 (myeloblast), HMEC (epithelium), HT-29 (colon), HUVEC (umbilical vein epithelium), Jurkat (T cell leukemia), JY (lymphoblastoid), K562 (lymphoblastoid), KBM-7 (lymphoblastoid), Ku812 (lymphoblastoid), KCL22 (lymphoblastoid), KGI (lymphoblastoid), KYO1 (lymphoblastoid), LNCap (prostate), Ma-Mel (melanoma), MCF-7 (mammary gland), MDF-10A (mammary gland), MDA-MB-231, -468 and -435 (breast), MG63 (osteosarcoma), MOR/0.2R (lung), MONO-MAC6 (white blood cells), MRCS (lung), NCI-H69 (lung), NALM-1 (peripheral blood), NW-145 (melanoma), OPCN/OPCT (prostate), Peer (leukemia), Raji (B lymphoma), Saos-2 (osteosarcoma), Sf21 (ovary), Sf9 (ovary), SiHa (cervical cancer), SKBR3 (breast carcinoma), SKOV-2 (ovary carcinoma), T-47D (mammary gland), T84 (lung), U373 (glioblastoma), U87 (glioblastoma), U937 (lymphoma), VCaP (prostate), WM39 (skin), WT-49 (lymphoblastoid), and YAR (B cell). Rodent cell lines of interest include but are not limited to 3T3 (mouse fibroblast), 4T1 (mouse mammary), 9L (rat glioblastoma), A20 (mouse lymphoma), ALC (mouse bone marrow), B16 (mouse melanoma), B35 (rat neuroblastoma), bEnd.3 (mouse brain), C2C12 (mouse myoblast), C6 (rat glioma), CGR8 (mouse embryonic), CT26 (mouse carcinoma), E14Tg2a (mouse embryo), EL4 mouse leukemia), EMT6/AR1 (mouse mammary), Hepalcic7 (mouse hepatoma), J558L (mouse myeloma), MC-38 (mouse adenocarcinoma), MTD-1A (mouse epithelium), RBL (rat leukemia), RenCa (mouse carcinoma), X63 (mouse lymphoma), YAC-1 (mouse Be cell), BHK-1 (hamster kidney), and CHO (hamster ovary). Plant cell lines of use include but are not limited to BY-2, Xan-1, GV7, GF11, GT16, TBY-AtRER1B, 3n-3, and G89 (tobacco); VR, VW, and YU-1 (grape); PAR, PAP, and PAW (pokeweed); Spi-WT, Spi-1-1, and Spi12F (spinach); PSB, PSW and PSG (sesame); A.per, A.pas, A.plo (asparagus); Pn and Pb (bamboo); and DG330 (soybean); embryonic cell lines; pluripotent cell lines; adult derived stem cells; reprogrammed cell lines; generic animal cell lines of any species or broadly embryonic or reprogrammed cells; zebra fish cell lines; primary dog cells; primary horse cells; chicken DT40 cells; dog cell lines; cat cell lines; patient cell lines; and, in some preferred embodiments, the HT1080 human cell line is utilized. Potential cells of use include any living cell, but those from eucaryotes are specifically contemplated. These cell lines and others are available from a variety of sources known to those with skill in the art (see, e.g., the American Type Culture Collection (ATCC) (Manassas, Va.)). A cell transfected with one or more vectors described herein is used to establish a new cell line that comprises one or more vector-derived sequences.

Synthetic Chromosome Production

The synthetic chromosomes of the present invention may be produced by any currently-employed methods of synthetic chromosome production. As discussed briefly, above, the real-time monitoring methods of the present invention are applicable to all of the "top down", "bottom up", engineering of minichromosomes, and induced de novo chromosome generation methods used in the art. The "bottom up" approach of synthetic chromosome formation relies on cell-mediated de novo chromosome formation following transfection of a permissive cell line with cloned α-satellite sequences, which comprise typical host cell-appropriate centromeres and selectable marker gene(s), with or without telomeric and genomic DNA. (For protocols and a detailed description of these methods see, e.g., Harrington, et al., Nat. Genet., 15:345-55 (1997); Ikeno, et al., Nat. Biotechnol., 16:431-39 (1998); Masumoto, et al., Chromosoma, 107:406-16 (1998), Ebersole, et al., Hum. Mol. Gene., 9:1623-31 (2000); Henning, et al., PNAS USA, 96:592-97 (1999); Grimes, et al., EMBO Rep. 2:910-14 (2001); Mejia, et al., Genomics, 79:297-304 (2002); and Grimes, et al., Mol. Ther., 5:798-805 (2002).) Both synthetic and naturally occurring α-satellite arrays, cloned into yeast artificial chromosomes, bacterial artificial chromosomes or P1-derived artificial chromosome vectors have been used in the art for de novo synthetic chromosome formation. The products of bottom up assembly can be linear or circular, comprise simplified and/or concatamerized input DNA with an α-satellite DNA based centromere, and typically range between 1 and 10 Mb in size. Bottom up-derived synthetic chromosomes also are engineered to incorporate nucleic acid sequences that permit site-specific integration of target DNA sequence onto the synthetic chromosome.

The "top down" approach of producing synthetic chromosomes involves sequential rounds of random and/or targeted truncation of pre-existing chromosome arms to result in a pared down synthetic chromosome comprising a centromere, telomeres, and DNA replication origins. (For protocols and a detailed description of these methods see, e.g., Heller, et al., PNAS USA, 93:7125-30 (1996); Saffery, et al., PNAS USA, 98:5705-10 (2001); Choo, Trends Mol. Med., 7:235-37 (2001); Barnett, et al., Nuc. Ac. Res., 21:27-36 (1993); Farr, et al., PNAS USA, 88:7006-10 (1991); and Katoh, et al., Biochem. Biophys. Res. Commun., 321:280-90 (2004).) "Top down" synthetic chromosomes are constructed optimally to be devoid of naturally-occurring expressed genes and are engineered to contain DNA sequences that permit site-specific integration of target DNA sequences onto the truncated chromosome, mediated, e.g., by site-specific DNA integrases.

A third method of producing synthetic chromosomes known in the art is engineering of naturally occurring minichromosomes. This production method typically involves irradiation-induced fragmentation of a chromosome containing a functional, e.g., human neocentromere possessing centromere function yet lacking α-satellite DNA sequences and engineered to be devoid of non-essential DNA. (For protocols and a detailed description of these methods see, e.g., Auriche, et al., EMBO Rep. 2:102-07 (2001); Moralli, et al., Cytogenet. Cell Genet., 94:113-20 (2001); and Carine, et a., Somat. Cell Mol. Genet., 15:445-460 (1989).) As with other methods for generating synthetic chromosomes, engineered minichromosomes can be engineered to contain DNA sequences that permit site-specific integration of target DNA sequences.

The fourth approach for production of synthetic chromosomes involves induced de novo chromosome generation by targeted amplification of specific chromosomal segments. This approach involves large-scale amplification of pericentromeric/ribosomal DNA regions situated on acrocentric chromosomes. The amplification is triggered by co-transfection of excess DNA specific to the percentric region of chromosomes, such as ribosomal RNA, along with DNA sequences that allow for site-specific integration of target DNA sequences and also a drug selectable marker which integrates into the pericentric regions of the chromosomes. (For protocols and a detailed description of these methods see, e.g., Csonka, et al., J. Cell Sci 113:3207-16 (2002); Hadlaczky, et al., Curr. Opini. Mol. Ther., 3:125-32 (2001); and Lindenbaum and Perkins, et al., Nuc. Ac. Res., 32(21): e172 (2004).) During this process, targeting to the pericentric regions of acrocentric chromosomes with co-transfected DNA induces large-scale chromosomal DNA amplification, duplication/activation of centromere sequences, and subsequent breakage and resolution of dicentric chromosomes resulting in a "break-off" satellite DNA-based synthetic chromosome containing multiple site-specific integration sites.

Component Delivery into the Synthetic Chromosome Production Cells

The vectors carrying the lineage reporter constructs of the present invention and/or the components appropriate for synthetic chromosome production can be delivered to the cells to be engineered and/or produce the synthetic chromosome by any method known in the art. The terms transfection and transformation refer to the taking up of exogenous nucleic acid, e.g., an expression vector, by a host cell whether or not any coding sequences are, in fact, expressed. Numerous methods of transfection are known to the ordinarily skilled artisan, for example, by *Agrobacterium*-mediated transformation, protoplast transformation (including polyethylene glycol (PEG)-mediated transformation, electroporation, protoplast fusion, and microcell fusion), lipid-mediated delivery, liposomes, electroporation, sonoporation, microinjection, particle bombardment and silicon carbide whisker-mediated transformation and combinations thereof (see, e.g., Paszkowski, et al., EMBO J., 3:2717-2722 (1984); Potrykus, et al., Mol. Gen. Genet., 199:169-177 (1985); Reich, et al., Biotechnology, 4:1001-1004 (1986); Klein, et al., Nature, 327:70-73 (1987); U.S. Pat. No. 6,143,949; Paszkowski, et al., in *Cell Culture and Somatic Cell Genetics of Plants*, Vol. 6, Molecular Biology of Plant Nuclear Genes, (Schell and Vasil, eds., Academic Publishers 1989); and Frame, et al., Plant J., 6:941-948 (1994)); direct uptake using calcium phosphate (Wigler, et al., Proc. Natl. Acad. Sci. U.S.A., 76:1373-1376 (1979)); polyethylene glycol (PEG)-mediated DNA uptake; lipofection (see, e.g., Strauss, Meth. Mol. Biol., 54:307-327 (1996)); microcell fusion (Lambert, Proc. Natl. Acad. Sci. U.S.A., 88:5907-5911 (1991); U.S. Pat. No. 5,396,767; Sawford, et al., Somatic Cell Mol. Genet., 13:279-284 (1987); Dhar, et al., Somatic Cell Mol. Genet., 10:547-559 (1984); and McNeill-Killary, et al., Meth. Enzymol., 254:133-152 (1995)); lipid-mediated carrier systems (see, e.g., Teifel, et al., Biotechniques, 19:79-80 (1995); Albrecht, et al., Ann. Hematol., 72:73-79 (1996); Holmen, et al., In Vitro Cell Dev. Biol. Anim., 31:347-351 (1995); Remy, et al., Bioconjug. Chem., 5:647-654 (1994); Le Bolch, et al., Tetrahedron Lett., 36:6681-6684 (1995); and Loeffler, et al., Meth. Enzymol., 217:599-618 (1993)); or other suitable methods. Methods for delivery of synthetic chromosomes also are described in U.S. application Ser. No. 09/815,979. Successful transfection is generally recognized by detection of the presence of the heterologous nucleic acid within the transfected cell, such as, for example, any visualization of the heterologous nucleic acid, expression of a selectable marker or any indication of the operation of a vector within the host cell. For a description of delivery methods useful in practicing the present invention, see U.S. Pat. Nos. 5,011,776; 5,747, 308; 4,966,843; 5,627,059; 5,681,713; Kim and Eberwine, Anal. Bioanal. Chem. 397(8): 3173-3178 (2010).

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1: Construction of a Synthetic Chromosome Containing Lineage Specific Reporters A synthetic chromosome has been successfully engineered to contain five lineage specific promoters linked to unique fluorescent reporters to provide a readout for cell lineage fate determination (i.e., a multifunctional cell-based biosensor). Briefly, a BAC backbone vector was constructed using IN-Fusion cloning (Clontech) to contain blasticidin drug resistance and attB sites necessary for λINTR recombination. The lineage specific promoters listed below were chosen, however, the present technology is amenable to potentially any promoter of interest: Oct4 (pluripotency), GATA4 (endoderm), Brachyury (mesoderm), and Otx2 (ectoderm). The selected promoters are well-characterized as described in the literature as markers of indicated cell lineages and have been used routinely in RT-PCR analysis of differentiated pluripotent stem cells and/or reporter linked assays. FLT1 was selected as a marker for brain endothelium (bEC) as it is enriched in bEC at the blood brain barrier. Each lineage specific promoter linked to a unique fluorescent marker followed by an SV40 polyadenylation signal was synthesized (GenScript) and cloned into pUC57-Kan. The length of each promoter was determined based on publications describing the activity of the promoter. PCR primers were designed to amplify the promoter/reporter cassette with each primer containing 5' tags for use in a single 6-way IN-Fusion cloning reaction. The resulting 19.2 Kbp vector was sequence verified prior to being loaded onto the synthetic chromosome. Drug resistant clones were isolated and successful engineering of the synthetic chromosome containing both site-specific recombination events (i.e., attP×attB recombination events) and all five of the cell lineage reporters was confirmed by PCR.

Example 2: Identification of Single Cells with Specific Lineage Phenotypes

Current labeling technologies limit the ability to track transplanted cells used in cell-based therapeutics. Indirect labeling technologies require in vitro labeling prior to transplantation. The most attractive features of stably labeling cells with fluorochromes using currently available technologies (i.e., propagation to daughter cells and signal being stoichiometric with cell mass) are associated with significant safety concerns (i.e., potential oncogenic effects of random genomic integration and each label requiring an independent integration event). The present synthetic chromosome technology circumvents these safety concerns by providing a stable, non-integrating, self-replicating and biocompatible intracellular platform with the bandwidth necessary to contain multiple labels while maintaining the benefits of current technologies. The lineage reporter synthetic chromosome is transferred into human iPSCs demonstrating the ability to identify cells of a particular lineage with single cell resolution within embryoid bodies. The experiments described in this Example use fluorescent markers suitable for in vitro analysis and demonstration of sensitivity and specificity. In vivo applications utilize appropriate reporters for analysis in whole organisms.

Transfer to iPSC:

The lineage reporter synthetic chromosome is isolated from DG44 cells by FACS following well-established protocols. The chromosome is transferred to human iPSCs cells using lipofectamine stem transfection reagent (ThermoFisher), an approach successfully used in the past to transfer synthetic chromosomes to human mesenchymal stem cells and murine embryonic stem cells. During synthetic chromosome transfer and the selection process, iPSCs cells are maintained as pluripotent cells and cultured in StemFlex Feeder-Free media (ThermoFisher). Drug resistant clones are screened by PCR for presence of lineage reporter sequences. Pluripotency of positive clones (up to 5) are confirmed based on morphology and expression of pluripotency markers, OCT4, Nanog, and LEFTY1, and analyzed by quantitative RT-PCR (qRT-PCR) using commercially available assays (ThermoFisher). The lineage reporter synthetic chromosome contains hrGFP expressed from the Oct4 promoter; therefore, confirmation is made that iPSCs containing the synthetic chromosome are GFP-positive. PCR and FISH confirms the integrity of the synthetic chromosome following transfer.

Differentiation of iPSCs into EBs:

Up to five iPSC clones derived above are differentiated into EBs, which are composed of heterogeneous populations both within and between EBs, using established protocols. EBs are assessed at day 4, day 7, and day 14 for expression of selected reporters. The visualization of the various reporter genes is tracked using a Zeiss LSM710 laser scanning confocal microscope set-up to detect the selected fluorescent protein markers. At each time point, EBs are dissociated using trypsin-EDTA and plated on coverslips. Once attached, the cells are analyzed by confocal microscopy. Comparison of the frequency of cellular phenotypes in 3-dimensional aggregates with those in dissociated cultures provides insight into the spatial resolution and sensitivity of the lineage reporter synthetic chromosome as a tool for single cell analysis within diverse populations.

Example 3: Purification of Single Cells of a Specific Lineage from a Diverse Population While progress has been made in developing protocols to create embryoid bodies and differentiate iPSCs, a major barrier to the use of human iPSCs in cell-based therapeutics is the ability to efficiently produce cells of specific lineages in a large scale, cost-effective manner. Microfluidic approaches to isolation and characterization of cell heterogeneity in EBs precludes downstream culture and utilization due to methodological requirement for cell fixation. The present invention demonstrates the benefit of the lineage reporter synthetic chromosome to efficiently isolate viable cells of a specific lineage from the diverse populations contained within embryoid bodies.

Differentiation of iPSC:

iPSCs will be differentiated as outlined in Example 2. The EBs are dissociated using trypsin-EDTA and then cells of each lineage isolated using flow sorting. Cultures of each lineage are established Immediately following sorting and at 24- and 48-hours post-sorting the degree of enrichment is assessed by microscopic imaging and quantitative RT-PCR to quantify expression of lineage specific markers. An aliquot of enriched cells from each of the three lineages (endo-, meso-, and ectoderm) is plated directly onto coverslips in a 35 $mm^2$ tissue culture plate and imaged using a Zeiss LSM710 laser scanning confocal microscope set-up to detect the selected fluorescent protein markers. After removal of the coverslip and immediate processing for microscopy, the remainder of the cells in the plate are used to isolate total RNA and used for qRT-PCR. Undifferentiated iPSCs are used as the baseline control for pluripotency genes while the brain endothelial cell marker FLT1-mCherry will be used as a negative control. Expression of 3 genes is assessed for each lineage using commercially available assays (ThermoFisher). All expression is normalized to expression of 18S rRNA. The lineage-specific genes that are assessed are: pluripotency—Nanog, Oct4, and LEFTY1; Endoderm—FoxA2, GATA6, SMAD2; Mesoderm—IGF2, SHH, NPPA; Ectoderm—Pax6, NCAM1, SOX1. Each culture will be assessed for all 12 genes to quantify relative expression of lineage specific markers over time in the enriched cultures.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. § 112, ¶16.

We claim:

1. A non-integrated, transferrable synthetic eukaryotic chromosome comprising:
   active centromeric and telomeric regions;
   replication origins;
   multiple site-specific recombination sequences; and
   a plurality of promoters, each promoter operably linked to a different reporter gene, wherein the promoters comprise an OTX2 promoter, a Brachyury promoter, a FLT1 promoter, a GATA4 promoter, and an OCT4 promoter.

* * * * *